US012018273B2

(12) United States Patent
Schaser et al.

(10) Patent No.: US 12,018,273 B2
(45) Date of Patent: Jun. 25, 2024

(54) CD62L SPECIFIC LENTIVIRAL VECTOR PARTICLE FOR TARGETED TRANSDUCTION OF T CELL SUBSETS

(71) Applicant: Miltenyi Biotec B.V. & Co. KG, Bergisch Gladbach (DE)

(72) Inventors: Thomas Schaser, Bergisch Gladbach (DE); Andrew Kaiser, Bergisch Gladbach (DE); Laura Kapitza, Bergisch Gladbach (DE); Jessica Hartmann, Bergisch Gladbach (DE); Frederic Thalheimer, Bergisch Gladbach (DE); Christian Buchholz, Bergisch Gladbach (DE)

(73) Assignee: Miltenyi Biorec B V. Co., KG, Bergisch Gladbach (DE)

( * ) Notice: Subject to any disclaimer, the term of this patent is extended or adjusted under 35 U.S.C. 154(b) by 60 days.

(21) Appl. No.: 17/465,734

(22) Filed: Sep. 2, 2021

(65) Prior Publication Data

US 2022/0064674 A1 Mar. 3, 2022

(30) Foreign Application Priority Data

Sep. 3, 2020 (EP) .................................. 20194232

(51) Int. Cl.
| | | |
|---|---|---|
| C12N 15/867 | (2006.01) | |
| C07K 14/005 | (2006.01) | |
| C07K 14/01 | (2006.01) | |
| C07K 16/28 | (2006.01) | |
| C12N 5/0783 | (2010.01) | |
| C12N 7/00 | (2006.01) | |
| C12N 15/86 | (2006.01) | |

(52) U.S. Cl.
CPC ............ *C12N 15/86* (2013.01); *C07K 14/005* (2013.01); *C07K 16/2854* (2013.01); *C12N 5/0636* (2013.01); *C12N 7/00* (2013.01); *C07K 2317/622* (2013.01); *C07K 2319/21* (2013.01); *C07K 2319/30* (2013.01); *C12N 2740/10043* (2013.01); *C12N 2760/18422* (2013.01)

(58) Field of Classification Search
None
See application file for complete search history.

(56) References Cited

U.S. PATENT DOCUMENTS

| 9,233,125 B2 | 1/2016 | Davila et al. |
| 9,862,971 B2 | 1/2018 | Buchholz et al. |
| 2021/0002610 A1* | 1/2021 | Alpert ............... C12N 5/0636 |
| 2021/0139932 A1* | 5/2021 | Lochrie ............... C07K 14/805 |
| 2021/0180083 A1 | 6/2021 | Schaser et al. |
| 2021/0283179 A1* | 9/2021 | Gill ..................... C07K 14/005 |
| 2021/0317408 A1* | 10/2021 | Frost ................. A61K 39/0011 |
| 2022/0025403 A1* | 1/2022 | Adair ..................... C12N 15/88 |
| 2022/0153826 A1* | 5/2022 | Keane ............... A61K 39/3955 |
| 2022/0362295 A1* | 11/2022 | Kieffer-Kwon ........................... C07K 14/70596 |

OTHER PUBLICATIONS

Bender et al., Receptor-Targeted Nipah Virus Glycoproteins Improve Cell-Type Selective Gene Delivery and Reveal a Preference for Membrane-Proximal Cell Attachment, Public Library of Science Pathogens, vol. 12, No. 6, Jun. 9, 2016, pp. 1-28.
Cordes et al., Anti-CD19 CARs Displayed at the Surface of Lentiviral Vector Particles Promote Transduction of Target-Expressing Cells, Molecular Therapy: Methods & Clinical Development, vol. 21, Jun. 2021, pp. 43-53.
Frank et al., Combining T-Cell-Specific Activation and In Vivo Gene Delivery Through CD3-Targeted Lentiviral Vectors, Blood Advances, vol. 4, No. 22, Nov. 24, 2020, pp. 5702-5715.
Jamali et al., Highly Efficient and Selective CAR-Gene Transfer Using CD4- and CD8-Targeted Lentiviral Vectors, Molecular Therapy: Methods & Clinical Development, vol. 13, Jun. 2019, pp. 371-379.
Tahara et al., Measles Virus Infects both Polarized Epithelial and Immune Cells by Using Distinctive Receptor-Binding Sites on Its Hemagglutinin, Journal of Virology, vol. 82, No. 9, May 2008, pp. 4630-4637.

* cited by examiner

*Primary Examiner* — Maria Marvich
(74) *Attorney, Agent, or Firm* — Kilpatrick Townsend & Stockton LLP

(57) ABSTRACT

The present invention provides a composition comprising i) a pseudotyped retroviral vector particle comprising a) one envelope protein with antigen-binding activity, wherein said envelope protein is a recombinant protein that does not interact with at least one of its original receptors and is fused at its ectodomain to a polypeptide comprising an antigen binding domain specific for CD62L, and wherein said envelope protein is protein G, HN or H derived from the Paramyxoviridae family, b) one envelope protein with fusion activity derived from the Paramyxoviridae family, and T cells expressing CD62L. Alternatively, when said polypeptide comprising an antigen binding domain is specific for a tag of a tagged polypeptide instead of the antigen binding domain specific for CD62L, wherein said tagged polypeptide binds specifically to CD62L, then the composition comprises further said tagged polypeptide.

14 Claims, 5 Drawing Sheets
Specification includes a Sequence Listing.

Selective transduction w. direct system

Selective transduction w. indirect, adapter system

CD62L SPECIFIC LENTIVIRAL VECTOR PARTICLE FOR TARGETED TRANSDUCTION OF T CELL SUBSETS

REFERENCE TO PREVIOUS APPLICATION

This application claims priority to European patent application No. 20194232.3 under the Paris Convention for the Protection of Industrial Property. The priority application is hereby incorporated herein by reference in its entirety for all purposes.

FIELD OF INVENTION

The present invention relates to the field of pseudotyped lentiviral vector particles for targeted transduction of T cells expressing CD62L, in particular to lentiviral vector particles having specificity for the CD62L antigen or to lentiviral vector particles having specificity for a tag, wherein said tag is coupled to a polypeptide that binds to the CD62L antigen, thereby allowing targeted transduction of T cells expressing said CD62L antigen.

BACKGROUND OF THE INVENTION

Lentiviral vectors are commonly used for transduction of e.g. T cells. For example, in the field of CAR T cell therapy, T cells are typically activated with polyclonal stimuli/agents to achieve sufficient gene transfer rates with lentiviral vectors and to obtain the cell doses required for therapeutic response in the patient. Activated T cells are efficiently transduced with lentiviral vectors pseudotyped with the G protein of vesicular stomatitis virus (VSV-G). The receptor of VSV-G has been described to be LDL-R incl. family members and to be sufficiently expressed on activated T cells. L-selectin, also known as CD62L, is a cell adhesion molecule found on leukocytes including lymphocytes, neutrophils, monocytes, eosinophils, and hematopoietic progenitor cells. On T cells, CD62L is expressed on non-activated (naïve) and/or central memory ($T_{CM}$) and/or stem cell memory ($T_{SCM}$) T cells. In contrast, effector memory ($T_{EM}$) and effector ($T_{EFF}$) T cells are negative for CD62L. CD62L contributes to leukocyte tethering and rolling along the luminal surface of venules and is cleaved off by proteases upon activation.

Gene transfer to non-activated T cells, i.e. resting T cells is becoming increasingly interesting for the following reasons:
  Less complicated and shorter manufacturing process;
  Less differentiated, less exhausted and more potent T cells.

Unfortunately, LDL-R is not expressed on non-activated T cells requiring alternative pseudotypes that mediate binding to abundantly expressed receptors. Chimeric and/or truncated versions of BaEV, RD114, GALV or measles envelope proteins have shown superior activity for non-activated T cells as compared to VSV-G. However, these pseudotypes have a broad tropism and therefore cannot selectively transduce specific T cells subsets. Currently, there is no pseudotype known in the art that is able to selectively transduce non-activated T cells with naïve and/or central memory ($T_{CM}$) and/or stem cell memory ($T_{SCM}$) phenotype.

There is a need in the art for an improved or alternative method of targeted transduction of T cell subsets using a lentiviral vector particle.

SUMMARY OF THE INVENTION

CD62L is expressed on resting (naïve) human T cells. The inventors surprisingly found that using a pseudotyped lentiviral vector particle having specificity for said CD62L antigen leads to efficient transduction of said resting T cells. The specificity may be achieved directly via a fusion envelope protein of the lentivirus vector particle with a CD62L-antigen-binding domain as disclosed herein or indirectly via a fusion envelope protein of said lentiviral vector particle with an antigen-binding domain specific for a tag of a tagged polypeptide, wherein said polypeptide may have a CD62L-antigen binding domain as disclosed herein.

Even more, it was surprisingly found that T cells expressing CD62L can be transduced with the pseudotyped lentiviral vector particle having specificity for said CD62L antigen as disclosed herein even in the presence of T cells shedding the extracellular domain of the CD62L receptor. It was unexpected that shed CD62L does not block the transduction of T cells with a pseudotyped lentiviral vector particle having specificity for said CD62L antigen as disclosed herein.

Compared to the state-of-the-art generation of CAR T cells by transducing activated T cells promising benefits of transducing resting (i.e. non-activated T cells) are that CAR T cells are less differentiated, less exhausted and more potent. In addition, the process of manufacturing CAR T cells based on non-activated T cells is less complicated and remarkably shorter than for the process with activated T cells.

In addition, a further benefit of the use of a pseudotyped lentiviral vector particle having specificity for said CD62L antigen as disclosed herein for transduction of a T cell composition is that subtypes of T cells are transduced only, namely naïve T cells, $T_{CM}$ and $T_{SCM}$. Effector T cells ($T_{EFF}$) and effector memory T cells ($T_{EM}$) are not transduced with the pseudotyped lentiviral vector particle having specificity for said CD62L antigen as disclosed herein as these cells do not express CD62L. This leads to a more valuable genetically engineered T cell composition compared to methods used in the prior art because $T_{SCM}$ and $T_{CM}$ have a greater therapeutic impact (efficacy) in a subject compared to $T_{EM}$ and $T_{EFF}$.

Even more surprisingly it was found that the use of a pseudotyped lentiviral vector particle having specificity for said CD62L antigen comprising the amino acid sequences as disclosed herein leads to outstanding transduction results of said resting T cells and/or $T_{CM}$ and/or $T_{SCM}$. Alternatively, the specificity for the CD62L antigen may be on the tagged polypeptide as disclosed herein, wherein said polypeptide may comprise a CD62L antigen binding domain.

DETAILED DESCRIPTION OF THE INVENTION

Figure 1:
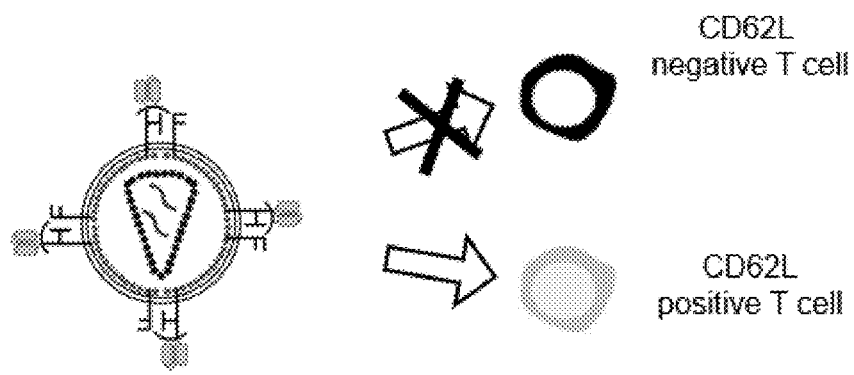
FIG. 1: Selective transduction of CD62L expressing cells with targeted lentiviral vectors either with a direct retroviral vector system or indirectly with an adaptable retroviral vector system.
Figure 1:
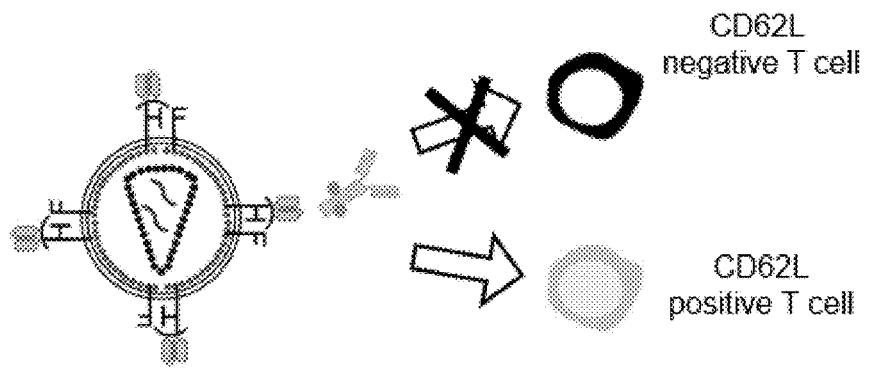
Figure 2:
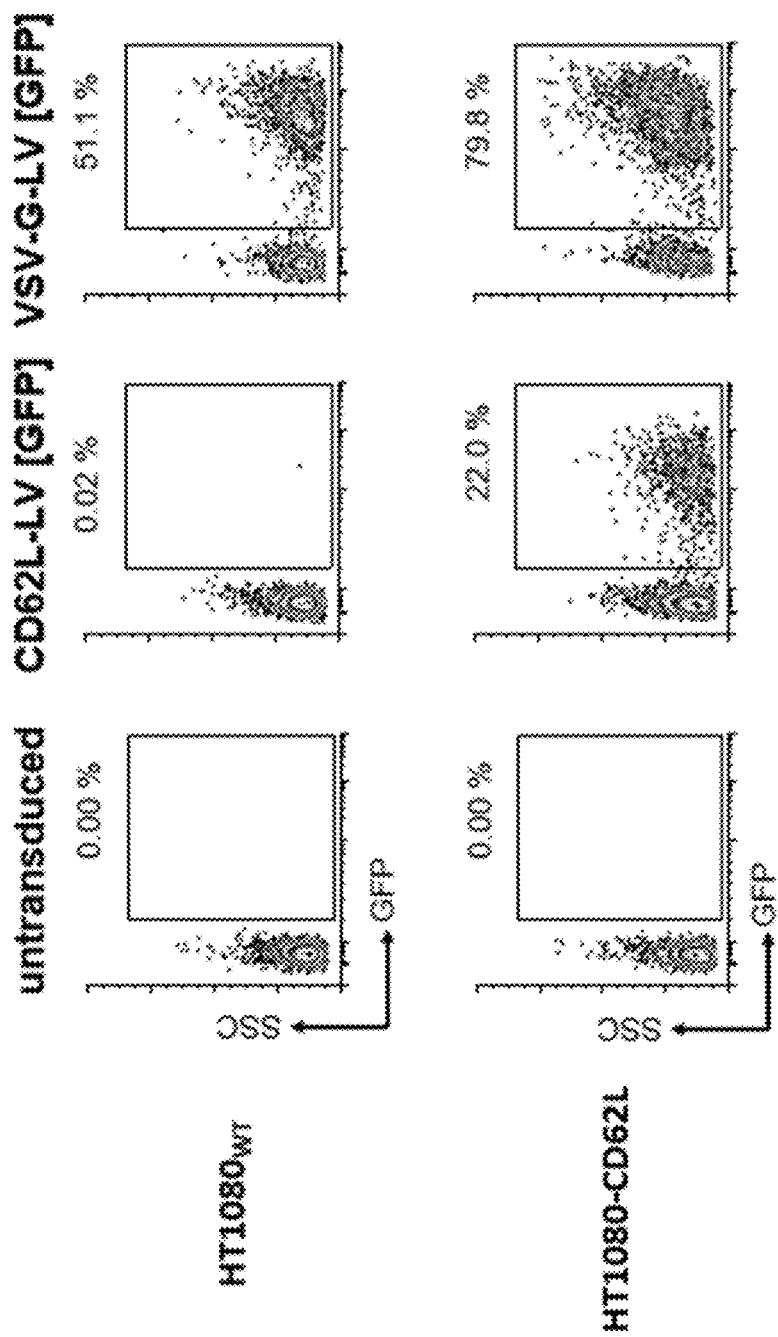
FIG. 2: Selectivity of CD62L-LV on HT1080 wt lacking CD62L or recombinant HT1080 expressing CD62L (HT1080-CD62L).

In a first aspect the present invention provides a composition (or a combination) comprising
i) a pseudotyped retroviral vector particle comprising
   a) one envelope protein with antigen-binding activity, wherein said envelope protein is a recombinant protein that does not interact with at least one of its original (native) receptors and is fused at its ectodomain to a polypeptide comprising an antigen binding domain specific for CD62L, and wherein said envelope protein is protein G, HN or H derived from the Paramyxoviridae family,
   b) one envelope protein with fusion activity derived from the Paramyxoviridae family, and
ii) T cells expressing CD62L.

Said composition as disclosed herein, wherein said composition may additionally comprise
iii) shed CD62L.

Said shed CD62L may comprise the extracellular domain of CD62L. Said shed CD62L may comprise or may consist of the amino acid sequence of SEQ ID NO:10.

Said composition as disclosed herein, wherein said T cells expressing CD62L may comprise $T_{CM}$ cells, and/or $T_{SCM}$ cells, and/or naïve T cells. Said composition as disclosed herein, wherein said composition may comprise $T_{CM}$ cells, $T_{SCM}$ cells, naïve T cells, $T_{EM}$ cells and $T_{EFF}$ cells. Regularly, these T cell subtypes are present in an enriched CD4+ and/or CD8+ T cell composition. As told, only $T_{CM}$ cells, $T_{SCM}$ cells and naïve T cells are effectively transduced by the pseudotyped retrovirus as disclosed herein.

Said composition as disclosed herein, wherein said Paramyxoviridae virus may be a virus of the Morbillivirus genus or of the Henipavirus genus.

Said composition as disclosed herein, wherein said protein derived from protein G, or H of a virus of the Paramyxoviridae family may lack at least one part of the cytoplasmic region of said protein G, or H. Such modifications are well known in the art and are described in more detail herein in the definition section.

Said composition as disclosed herein, wherein said envelope protein with fusion activity derived from the Paramyxoviridae family may lack at least one part of the cytoplasmic region of said envelope protein. Such modifications are well known in the art and are described in more detail herein in the definition section.

Said composition as disclosed herein, wherein said Morbillivirus may be a measles virus or the Edmonston strain of measles virus. Said composition as disclosed herein, wherein said retroviral vector particle may be a lentiviral or gammaretroviral vector particle.

Said composition as disclosed herein, wherein said antigen binding domain specific for CD62L may be a scFv. Said composition as disclosed herein, wherein said antigen binding domain specific for CD62L may comprise the amino acid sequences of SEQ ID NO:1, SEQ ID NO:2, SEQ ID NO:3, SEQ ID NO:4, SEQ ID NO:5 and SEQ ID NO:6. Said composition as disclosed herein, wherein said antigen binding domain specific for CD62L may comprise the amino acid sequence of SEQ ID NO:7 and SEQ ID NO:8. Said composition as disclosed herein, wherein said antigen binding domain specific for CD62L may comprise the amino acid sequence of SEQ ID NO:9.

Said composition as disclosed herein, wherein said retroviral vector particle may comprises a nucleic acid encoding a transgene. Said composition as disclosed herein, wherein said transgene may be a chimeric antigen receptor.

In another aspect the present invention provides a composition comprising
i) a pseudotyped retroviral vector particle comprising
   a) one envelope protein with antigen-binding activity, wherein said envelope protein is a recombinant protein that does not interact with at least one of its original (native) receptors and is fused at its ectodomain to a polypeptide comprising an antigen binding domain specific for a tag of a tagged polypeptide, and wherein said envelope protein is protein G, HN or H derived from the Paramyxoviridae family,
   b) one envelope protein with fusion activity derived from the Paramyxoviridae family,
ii) T cells expressing CD62L,
iii) said tagged polypeptide, wherein said tagged polypeptide binds specifically to CD62L.

Said composition as disclosed herein, wherein said composition additionally may comprise: iv) shed CD62L. Said shed CD62L may comprise the extracellular domain of CD62L. Said shed CD62L may comprise or may consist of the amino acid sequence of SEQ ID NO:10.

Said tag of said tagged polypeptide may be not expressed on any cell of any species (target cells and non-target cells) of a subject or of a cell culture in which said retroviral vector particle may be applied for transduction, e.g. in a human. As a consequence, said retroviral vector particle may transduce any target cell in the presence of said tagged polypeptide only. The non-target cells furthermore are not transduced in the presence of said tagged polypeptide.

The tag of said tagged polypeptide may be a hapten. Said hapten may be selected from the group consisting of biotin, fluorescein isocyanate (FITC), fluorescein, NHS-fluorescein, 2,4-dinitrophenol (DNP), digoxigenin, thiamin and dextran. Said hapten may be biotin.

Said composition as disclosed herein, wherein said T cells expressing CD62L may comprise TCM cells, and/or TSCM cells, and/or naïve T cells. Said composition as disclosed herein, wherein said composition may comprise $T_{CM}$, $T_{SCM}$ cells, naïve T cells, $T_{EM}$ cells and $T_{EFF}$ cells. Regularly, these T cell subtypes are present in an enriched CD4+ and/or CD8+ T cell composition.

Said composition as disclosed herein, wherein said Paramyxoviridae virus may be a virus of the Morbillivirus genus or of the Henipavirus genus. Said composition as disclosed herein, wherein said protein derived from protein G, or H of a virus of the Paramyxoviridae family may lack at least one part of the cytoplasmic region of said protein G, or H.

Said composition as disclosed herein, wherein said envelope protein with fusion activity derived from the Paramyxoviridae family may lack at least one part of the cytoplasmic region of said envelope protein.

Said composition as disclosed herein, wherein said Morbillivirus may be a measles virus or the Edmonston strain of measles virus. Said composition as disclosed herein, wherein said retroviral vector particle may be a lentiviral or gammaretroviral vector particle.

Said composition as disclosed herein, wherein said antigen binding domain specific for CD62L may be a scFv. Said composition as disclosed herein, wherein said antigen binding domain specific for CD62L may be a DARPin.

Said composition as disclosed herein, wherein said tagged polypeptide may comprise an antigen binding domain specific for CD62L, e.g. said polypeptide may be an antibody or antigen binding fragment thereof.

Said composition as disclosed herein, wherein said antigen binding domain of said tagged polypeptide specific for CD62L may comprise the amino acid sequences of SEQ ID NO:1, SEQ ID NO:2, SEQ ID NO:3, SEQ ID NO:4, SEQ ID NO:5 and SEQ ID NO:6.

Said composition as disclosed herein, wherein said antigen binding domain of said tagged polypeptide specific for CD62L may comprise the amino acid sequence of SEQ ID NO:7 (VL) and SEQ ID NO:8 (VH). The orientation may be SEQ ID NO:7 (VL)-linker-SEQ ID NO:8 (VH) or SEQ ID NO:8 (VH)-linker-SEQ ID NO:7 (VL). Linkers for linking VL and VH domains are well known in the art and may be e.g. a (G45)3 linker or a (G45)4 linker. Said composition as disclosed herein, wherein said antigen binding domain of said tagged polypeptide specific for CD62L may comprise the amino acid sequence of SEQ ID NO:9.

Said composition as disclosed herein, wherein said retroviral vector particle may comprises a nucleic acid encoding a transgene. Said composition as disclosed herein, wherein said transgene may be a chimeric antigen receptor.

In another aspect the present invention provides a pseudotyped retroviral vector particle comprising:

a) one envelope protein with antigen-binding activity, wherein said envelope protein is a recombinant protein that does not interact with at least one of its original (native) receptors and is fused at its ectodomain to a polypeptide comprising an antigen binding domain specific for CD62L, and wherein said envelope protein is protein G, HN or H derived from the Paramyxoviridae family,
b) one envelope protein with fusion activity derived from the Paramyxoviridae family.

In another aspect the present invention provides a composition comprising i) a pseudotyped retroviral vector particle comprising
    a) one envelope protein with antigen-binding activity, wherein said envelope protein is a recombinant protein that does not interact with at least one of its original (native) receptors and is fused at its ectodomain to a polypeptide comprising an antigen binding domain specific for a tag of a tagged polypeptide, and wherein said envelope protein is protein G, HN or H derived from the Paramyxoviridae family,
    b) one envelope protein with fusion activity derived from the Paramyxoviridae family,
ii) said tagged polypeptide, wherein said tagged polypeptide binds specifically to CD62L.

In a further aspect the present invention provides an in vitro method for transduction of target cells, wherein said target cells are T cells expressing CD62L, the method comprising the step: addition of a pseudotyped retroviral vector particle to said target cells, wherein said pseudotyped retroviral vector comprises a) one envelope protein with antigen-binding activity, wherein said envelope protein is a recombinant protein that does not interact with at least one of its original (native) receptors and is fused at its ectodomain to a polypeptide comprising an antigen binding domain specific for CD62L, and wherein said envelope protein is protein G, HN or H derived from the Paramyxoviridae family,
b) one envelope protein with fusion activity derived from the Paramyxoviridae family.

In a further aspect the present invention provides an in vitro method for transduction of target cells, wherein said target cells are T cells expressing CD62L, the method comprising the steps:

i) addition of a pseudotyped retroviral vector particle to said target cells, wherein said pseudotyped retroviral vector comprises
    a) one envelope protein with antigen-binding activity, wherein said envelope protein is a recombinant protein that does not interact with at least one of its original (native) receptors and is fused at its ectodomain to a polypeptide comprising an antigen binding domain specific for a tag of a tagged polypeptide, and wherein said envelope protein is protein G, HN or H derived from the Paramyxoviridae family,
    b) one envelope protein with fusion activity derived from the Paramyxoviridae family, and
ii) addition of said tagged polypeptide to said target cells, wherein said tagged polypeptide binds specifically to CD62L.

The addition of said pseudotyped retroviral vector to said target cells may be performed before, after or simultaneously to the addition of said tagged polypeptide to said target cells.

In a further aspect the present invention provides the use of a pseudotyped retroviral vector particle for transducing T cells expressing CD62L, the pseudotyped retroviral vector particle comprising a) one envelope protein with antigen-binding activity, wherein said envelope protein is a recombinant protein that does not interact with at least one of its original (native) receptors and is fused at its ectodomain to a polypeptide comprising an antigen binding domain specific for CD62L, and wherein said envelope protein is protein G, HN or H derived from the Paramyxoviridae family,
b) one envelope protein with fusion activity derived from the Paramyxoviridae family.

In a further aspect the present invention provides the use of a composition (or combination) for transducing T cells expressing CD62L, the composition comprising
i) a pseudotyped retroviral vector particle comprising
a) one envelope protein with antigen-binding activity, wherein said envelope protein is a recombinant protein that does not interact with at least one of its original (native) receptors and is fused at its ectodomain to a polypeptide comprising an antigen binding domain specific for a tag of a tagged polypeptide, and wherein said envelope protein is protein G, HN or H derived from the Paramyxoviridae family,
b) one envelope protein with fusion activity derived from the Paramyxoviridae family,
ii) said tagged polypeptide, wherein said tagged polypeptide binds specifically to CD62L.

All definitions, characteristics and embodiments defined herein with regard to the first aspect of the invention as disclosed herein also apply mutatis mutandis in the context of the other aspects and embodiments of the invention as disclosed herein. In addition to above described applications and embodiments of the invention further embodiments of the invention are described in the following without intention to be limited to these embodiments.

EMBODIMENTS

In a preferred embodiment of the invention CD62L positive T cells are selectively transduced with a retroviral vector particle as disclosed herein in a mixed cell population containing CD62L positive and CD62L negative T cells.

The mixed cell population comprising T cells may be provided from a human e.g. patient suffering from cancer. CD4+ and/or CD8+ T cells may be enriched by a magnetic separation step using anti-CD4 and/or anti-CD8 antibodies or antigen binding fragments thereof coupled to a magnetic particle.

In a preferred embodiment the enriched CD4+ and/or CD8+ T cells are not activated with polyclonal activation reagents. In a preferred embodiment the enriched T cells have a naïve, central memory and/or stem cell memory phenotype. In another embodiment the genetically modified T cells were generated in equal or less than 72 hours, less than 48 hours, or less than 24 hours.

In another embodiment of the invention, the expansion of the genetically modified T cells in the generated sample is less than 10-fold, less than 5-fold, less than 2-fold, less than 1-fold compared to the amount of T cells of the originally provided sample comprising T cells.

In another embodiment of the invention, the CD62L positive T cells are genetically engineered with retroviral vector particles as disclosed herein encoding chimeric antigen receptor (CAR) or TCR and the application may be for treating cancer in a patient.

In another embodiment of the invention, T cells are genetically modified by the methods as disclosed herein in a closed system in an automated process, e.g. by using the CliniMACS® Prodigy (Miltenyi Biotec) to express a chimeric antigen receptor.

In another embodiment of the invention an adaptable retroviral vector system as disclosed herein is used, wherein said retroviral vector particle can bind to a tag and the corresponding tagged polypeptide binds specifically to CD62L. In another embodiment of the adaptable retroviral vector system the transduction efficiency is controlled by varying the amount of said tagged polypeptide.

In another embodiment of the invention CD62L positive T cells of a mixed cell population are transduced with the retroviral vector particle as disclosed herein that encodes a marker gene, thereby enabling identification and/or isolation of T cells of naïve, central memory or stem cell memory phenotype in a mixed cell population.

Definitions

Unless defined otherwise, technical and scientific terms used herein have the same meaning as commonly understood by one of ordinary skill in the art to which this invention belongs.

As used herein the term "comprising" or "comprises" is used in reference to compositions, methods, and respective component(s) thereof, that are essential to the method or composition, yet open to the inclusion of unspecified elements, whether essential or not.

Retroviridae is a virus family with a single-stranded, diploid, positive-sense RNA genome that is reverse-transcribed into a DNA intermediate that is then incorporated into the host cell genome. Retroviridae-derived viruses are enveloped particles with a diameter of 80-120 nm.

(Retro-/lenti-/gammaretro-) viral vectors are replication-deficient viral particles that are derived from the corresponding virus family. They contain Gag and Pol proteins, a single-stranded RNA genome and are usually pseudotyped with heterologous envelope proteins derived from other viruses. The RNA genome of said viral vectors do not contain any viral gene to produce viral progeny, but psi elements and LTRs that are required for efficient packing and reverse transcription into DNA. The DNA intermediate may contain a gene of interest under the control of a suitable promoter, for example, the CMV promoter and the gene of interest is expressed upon integration of said DNA into the genome of the host cell. The process of entering the host cell, delivering the RNA genome, integration and expression of the gene of interest is called transduction. The minimal requirements of a gammaretrovirus or lentivirus based viral vector has been well-described in the art.

In addition, integrase-deficient retroviral vectors (ID-RVs) have been developed that cannot integrate the retroviral vector genome in the host cell genome. ID-RVs are derived from conventional retroviral vectors but contain no or a mutated form of the retroviral integrase. Upon entry into the host cell, the retroviral vector genome is reverse-transcribed in the cytoplasm, delivered into the nucleus, but not stably integrated into the host cell genome. ID-RVs are useful tools to express the gene of interest transiently. The definition of retroviral vectors and transduction also extents the integration-deficient retroviral vectors and its application.

Lentivirus is a genus of Retroviridae that cause chronic and deadly diseases characterized by long incubation periods, in the human and other mammalian species. The best-known lentivirus is the Human Immunodeficiency Virus (HIV), which can efficiently infect nondividing cells, so lentiviral derived retroviral vectors are one of the most efficient methods of gene delivery.

Gammaretroviridae is a genus of the Retroviridae family. Representative species are the murine leukemia virus (MLV) and the feline leukemia virus (FLV).

Paramyxoviridae is a family of viruses in the order of Mononegavirales. There are currently 49 species in this family, divided among 7 genera. Diseases associated with this virus family include measles, mumps, and respiratory tract infections. Members of this virus family are enveloped viruses with a non-segmented, negative-strand RNA genome of about 16 kb. Two membrane proteins with two distinct functions appear as spikes on the virion surface. The H/HN/G proteins mediate binding to the receptor at the cell surface.

Thus, the term "(virus) envelope protein(s) that have antigen binding activity" as used herein refers to protein(s) on the viral envelope that are responsible for binding to complementary receptors or antigens on the cell membrane of a target cell. For Paramyxoviridae H, HN or G proteins are virus envelope protein(s) that have antigen binding activity.

Upon binding the H/HN/G proteins change their conformation that induces a process called fusion helper function, leading to subsequent conformational changes within the F protein that is mediating the fusion of the viral and cellular membrane. The capsid and viral genome may now enter and infect or transduce the host cell.

The term "(virus) envelope proteins(s) that have fusion activity" as used herein refers to protein(s) that initiate fusion of viral and cellular membrane. For Paramyxoviridae F proteins refer to virus envelope protein(s) that have fusion activity.

The term "ectodomain" or "extracellular part/domain" as used herein refers to a domain of a membrane protein that extends into the extracellular space (the space outside a cell or virion).

The term "activation" as used herein refers to inducing physiological changes of a cell that increase target cell function, proliferation and/or differentiation.

The term "non-activated" as used herein refers to T cells that are not activated or have not been fully activated via signal 1 (an antigen-specific signal provided by the binding of the TCR to antigenic peptide complexed with MHC.TCR binding) and signal 2 (CD28 costimulatory signal). Thus, signal 1 and signal 2 are absent in such non-activated T cells, whereas the presence of signal 3 (the presence of cytokines) is optional.

The term "pseudotyping" or "pseudotyped" as used herein refers to a vector particle bearing envelope glycoproteins derived from other viruses having envelopes. The host range of the lentiviral vectors or vector particles of the present invention can thus be expanded or altered depending on the type of cell surface receptor used by the glycoprotein.

To generate retroviral vectors the gag, pol and env proteins needed to assemble the vector particle are provided in trans by means of a packaging cell line, for example, HEK-293T. This is usually accomplished by transfection of the packaging cell line with one or more plasmids containing the gag, pol and env genes. For the generation of pseudotyped vectors, the env gene, originally derived from the same retrovirus as the gag and pol genes and as the RNA molecule or expression vector, is exchanged for the envelope protein(s) of a different enveloped virus. As an example, the F and H or HN or G protein of Paramyxoviridae is used.

Thus, an exemplary pseudotyped vector particle based on the HIV-1 retrovirus comprises the (1) HIV-1 Gag and Pol proteins, (2) an RNA molecule derived from the HIV-1 genome that may be used to generate a retroviral vector particle based on the HIV-1 genome lacking the gag, env, pol, tat, vif, vpr, vpu and nef genes, but still comprising the LTRs, the psi element and a CMV promoter followed by the gene to be transduced, for example, a gene for the GFP protein, and (3) the F and H proteins of measles virus, for example, in a truncated form.

The terms "native receptor" or "originally receptor" as used herein may be used interchangeably and refer to the receptor or antigen expressed on the cell surface of a cell that is bound by the naturally occurring virus envelope protein with antigen (receptor) binding activity. The native measles virus receptors are SLAM, nectin-4 and CD46. Nipahvirus envelope proteins use ephrin-B2 and ephrin-B3 as receptors for entry.

Reduced interaction means that said truncated and/or mutated protein interacts with said at least one native receptor at least 50% less efficient, at least 60% less efficient, at least 70% less efficient, at least 80% less efficient, at least 90% less efficient, at least 95% less efficient, at least 99% less efficient compared to the non-mutated protein. Preferentially said protein does not interact anymore with said at least one of its native receptors. The interaction may be the binding of these two molecules to each other. The less efficient interaction may be a reduced affinity of said protein to its native receptor. Said envelope protein with antigen-binding activity may have more than one native receptors, then the reduction or ablation of interaction of one of these native receptors of said protein results in a reduced tropism of the vector particle. The more interactions of said protein with its native receptors are inhibited by mutation the more effective is the reduction of tropism of the vector particle.

In some cases it may be sufficient to inhibit the interaction of some but not all native receptors to said protein as the remaining interactions are not of relevance in the intended application or use of the retroviral vector particle as disclosed herein, e.g. when a native receptor is not expressed on any cell (target cells and non-target cells) in the environment of target cells that are intended to be transduced.

If an envelope protein with antigen-binding activity has more than 2 native receptors, e.g. 3 native receptors, then preferentially said protein does not interact with the majority of its native receptors, e.g. 2 from 3. More preferentially, the envelope protein with antigen-binding activity does not interact with all of its native receptors.

The term "tropism" as used herein refers to the host range or specificity of a virus or retroviral vector. As used herein, the envelope protein with antigen-binding activity that is fused at its ectodomain to a polypeptide comprising an antigen binding domain defines the host range of the retroviral vector. For the adaptable retroviral vector system, the tagged polypeptide specific for antigen expressed on target cells defines the host range of the retroviral vector.

The term "target cell" as used herein refers to a cell which expresses an antigen (a marker) on its cell surface that should be recognized (bound) by the pseudotyped retroviral vector particle as disclosed herein or the tagged polypeptide of the adaptable system as disclosed herein, regularly the target cell is a T cell expressing CD62L. The target cell may be a eukaryotic primary cell or a cell line. The target cell may be a mammalian cell such as a murine cell, preferentially the target cell is a human cell. The term "non-target cells" as used herein refers to a cell which does not express CD62L and therefore is not bound and transduced by said retroviral vector particles.

The term "selective" and "targeted" as used herein refer to retroviral vector particles that induce preferential transduction in target cells. Thus, the transduction with pseudotyped retrovirus vector particles is 10-fold higher, preferentially 100-fold higher, most preferentially 1000-fold higher on said target cells than on non-target cells. In the present invention this is achieved by incubating cells with the pseudotyped retroviral vector as disclosed herein or the tagged polypeptide in the presence of a pseudotyped retroviral vector that comprises an envelope protein with antigen binding activity with reduced or ablated interaction with its native receptor(s) and a fusion polypeptide comprising an antigen binding domain specific for a tag of a tagged polypeptide at the ectodoman of said envelope protein. For Paramyxoviridae H/HN and G proteins are proteins with antigen binding activity.

Thus, the tropism of a selective or targeted retroviral vector particle of the present invention is not defined by the tropism of the virus the G, HN or H protein is derived from, but, depending on the specificity of the envelope protein that is a recombinant protein that does not interact with at least one of its original receptors and is fused at its ectodomain to a polypeptide comprising an antigen binding domain specific for CD62L or specific for a tag as disclosed herein, for a cell surface antigen, i.e. herein CD62L, of a target cell.

For selective retroviral vector particle pseudotyped with measles virus envelope proteins, the truncated protein H fused to the polypeptide comprising an antigen binding domain specific for CD62L or a tag of a tagged polypeptide as disclosed herein must have mutations that generally reduce or ablate productive interactions with its native receptors. Such mutations are well-known in the art. A mutation that ablates interaction of measles H protein with CD46 is e.g. the point mutation at position Y481, F431, V451, Y452, A527, P486, I487, A428, L464, G546, S548, F549 wherein these amino acids are replaced with another amino acid and this mutation prevents or assists in preventing interaction of the H protein with CD46. Alternatively, replacement of all five consecutive residues 473 to 477 in H protein with alanine may prevent interaction of H protein with CD46. Any of the above cited mutations maybe combined with each other For example, the following introduction of mutations ablates productive interaction of the measles H protein with CD46 and SLAM, respectively: Y481A R533A. (Nakamura et al. (2004), Nakamura et al. (2005), Vongpunsawad et al. (2004), Masse et al. (2002), Masse et al. (2004), Patterson et al. (1999)). In another embodiment, the Hmut protein also includes the mutations S548L and F549S, which lead to a more complete ablation of residual infectivity via CD46. Also, the mutation of the residues V451 and Y529 ablates productive interaction with CD46 and SLAM. Alternative mutations for ablating/preventing interaction of the H protein with CD46 have been described above. All of these mutations, which are introduced into the truncated H proteins in order to reduce or ablate the natural receptor usage, are located in the ectodomain of the measles H protein. For preventing interaction of the H protein with SLAM one of the following residues may be replaced with any other amino acid, in particular, alanine: I194, D530, Y553, T531, P554, F552, D505, D507.

For nectin-4, mutations within the H protein have been proposed in the art which abolish binding to this receptor as well. For example, Tahara et al. show that amino acid substitutions F483A, Y541S and Y543S of wt measles virus H protein result in an ablated fusion activity on Nectin-4 positive cells (Tahara et al. (2008)). This has been confirmed by Liu et al. showing that amino acid substitutions F543A and P497S of the Edmonston strain H abolish infection by vesicular stomatitis virus pseudotyped with Edmonston strain F and H envelope proteins (Liu et al. (2014)). There are further residues on the surface of the H molecule which are well conserved among different Morbilliviruses that may be involved in Nectin-4 dependent fusion, e.g. Phe483, Asp521, Leu522, Tyr524, Tyr541, Tyr543, Ser544, Arg547, Ser550, and Tyr551 (Tahara et al. (2008)). This suggests that further mutations might be helpful for preventing interaction with Nectin-4. Lentiviral or gammaretroviral vector particles pseudotyped with truncated F proteins and mutated H proteins additionally displaying at their ectodomain a polypeptide comprising an antigen binding domain specific for CD62L or a tag of a tagged polypeptide, wherein said tagged polypeptide binds specifically to CD62L, no longer enter cells via CD46, SLAM and/or nectin-4, but are rather targeted to and enter only those cells displaying the respective corresponding markers, i.e. CD62L, at their surface.

For selective retroviral vector particles pseudotyped with Nipahvirus envelope proteins reduced or ablated interactions of the G protein to the native receptors ephrin-B2 and ephrin-B3 is required. Residues within the G protein were identified by screening mutants resulting in variants with ablated receptor binding ability (Bender et al. (2016)). E501, W504, Q530, E533 were either single mutated or in combination. The combined mutation of E501A, W504A, Q530A, E533A showed completely ablated receptor binding ability for both receptors ephrin-B2 and ephrin-B3.

A pseudotyped retroviral vector particle "derived from", for example, HIV-1, as used in the present invention, refers to a particle in which the genetic information for the RNA and/or the Gag and Pol proteins comprised by the vector particle originate from said retrovirus, in the above case, HIV-1. The original retroviral genome can comprise mutations, such as deletions, frame shift mutations and insertions.

The terms "cytoplasmic portion", "cytoplasmic tail", "cytoplasmic region", "intracellular domain" or "endodomain", as used in herein refer to the portion of the respective protein that is adjacent to the transmembrane domain of the protein and, if the protein is inserted into the membrane under physiological conditions, extends into the cytoplasm or in case of viral particles reaching into the intravirion side. Within Paramyxoviridae all envelope proteins with antigen-binding function are characterized to date as type II membrane proteins, meaning that the cytoplasmic domain is located at the N-terminus of the envelope protein.

For the measles F protein, the transmembrane domain is identified by five amino acid sequence (SEQ ID NO:11), for the measles H protein, the domain is identified by four amino acid sequence (SEQ ID NO:12). The cytoplasmic portion of the measles F protein usually consists of the 33 C-terminal amino acids, the sequence for measles Edmonston strain can be found in SEQ ID NO:13. The cytoplasmic portion of the measles H protein typically consists of 34 N-terminal amino acids, the sequence for measles Edmonston strain can be found in SEQ ID NO:14.

For the Nipah G protein, the transmembrane domain is usually identified by the amino acid sequence as shown in SEQ ID NO:15 and cytoplasmic portion as shown in SEQ ID NO:16. For the Nipah F protein, the transmembrane domain is usually defined by the amino acid sequence as shown in SEQ ID NO:17 and the cytoplasmic portion usually consists of the amino acid sequence as shown in SEQ ID NO:18.

The term "truncated", as used in the present invention, refers to a deletion of amino acid residues of the designated protein. It is clear to the skilled person that a protein is encoded by a nucleic acid. Thus, "truncated" also refers to the corresponding coding nucleic acids in a nucleic acid molecule that codes for a given "truncated" protein.

Furthermore, it is to be understood that the nucleic acid molecules encoding for a specific truncated or modified protein are likewise encompassed, and vice versa.

In the present invention, specific reference is made to "truncated H", "truncated G" or "truncated F" proteins, which designates the Paramyxoviridae, preferably measles H protein, Nipah G protein and Nipah or measles F proteins, respectively, whose cytoplasmic portion has been partly or completely truncated, i.e. amino acid residues (or coding nucleic acids of the corresponding nucleic acid molecule encoding the protein) have been deleted. The cytoplasmic portion of the F protein is located at the C-terminus of the protein.

For all envelope protein with the cytoplasmic portion located at the C-terminus one begins counting from the C-terminal end of the protein when ascertaining the desired sequence. As an example, for the F protein derived from measles Edmonston strain FcΔ30 would refer to an F protein having a cytoplasmic portion with the amino acid sequence "RGR". By contrast, the cytoplasmic portion of the H, HN or G protein is located at the N-terminus.

Thus, one begins counting at the second amino acid residue of the N-terminal end of the H, HN or G protein (i.e. omitting the first methionine residue) when ascertaining the desired sequence.

It is disclosed in WO2008037458A2 that the cytoplasmic domain of the measles F protein can be truncated to comprise at least 1 positively charged amino acid residue and the cytoplasmic portion of the H protein can be truncated to comprise at least 9 consecutive amino acid residues of the C-terminal cytoplasmic portion of the H protein plus an additional methionine at the N-terminus. However, a further truncation of the cytoplasmic portion of the H protein is expected to be feasible, if the H protein is truncated to allow efficient pseudotyping and still has fusion support function.

Modifications that allow truncation for efficient pseudotyping may be combined with modifications that ablate native receptor binding function. The person skilled in the art will readily be able to introduce mutations as, for example, additions and deletions, into a given nucleic acid or amino acid sequence.

The proteins of the present invention further include functional homologs. A protein is considered a functional homolog of another protein for a particular function, if the homolog has a similar function as the original protein. The homolog can be, for example, a fragment of the protein, or a substitution, addition, or deletion mutant of the protein.

Determining whether two amino acid sequences are substantially homologous is typically based on FASTA searches. For example, the amino acid sequence of a first protein is considered to be homologous to that of a second protein if the amino acid sequence of the first protein shares at least about 70% amino acid sequence identity, preferably at least about 80% identity, and more preferably at least about 85%, 90%, 95% or 99% identity, with the sequence of the second protein.

The terms "Psi positive" and "psi negative", as used in the present application, refer to a nucleic acid molecule where the retroviral psi element is present and absent, respectively. The psi element is a cis-acting signal located near the 5' end of the retroviral genome and designates a packaging signal, which is of importance during assembly of the viruses and leads to the incorporation of the viral RNA into the viral core. Thus, a psi negative RNA does not comprise the retroviral psi element and consequently will not be assembled into a vector particle of the present invention; in contrast, a psi positive RNA that does comprise said psi element will be effectively assembled into the vector particle.

The terms "Titer" or "transduction efficiency" are used as a means to characterize and compare vector particles with regard to their ability to transduce their target cells. Thus, vector particles having an "increased titer" or an "increased transduction efficiency" are able to transduce a higher number of cells at a given vector particle volume than other vector particles with the same volume.

The term "antigen expressed on the surface of a (target) cell" or "cell (surface) marker", as used in the present invention, refers to a molecule present on the surface of a cell, preferentially on a target cell. Such molecules can be, inter alia, peptides or proteins that may comprise sugar chains or lipids, clusters of differentiation (CDs), antibodies or receptors. Since not all populations of cells express the same cell markers, a cell marker can thus be used to identify, select or isolate a given population of cells expressing a specific cell marker. As an example, CD4 is a cell marker expressed by T helper cells, regulatory T cells, and dendritic cells. Thus, T helper cells, regulatory T cells, and dendritic cells can be identified, selected or otherwise isolated, inter alia by a FACS cell sorter, by means of the CD4 cell marker.

The term "tagged polypeptide" that is specific for binding to CD62L as used herein refers to a polypeptide that has bound thereto directly or indirectly at least one additional component, i.e. the tag. The tagged polypeptide as used herein is able to bind an antigen expressed on a target cell, herein CD62L on T cells expressing CD62L. The polypeptide may be an antibody or antigen binding fragment thereof that binds to said antigen expressed on the surface of a target cell. The polypeptide of the tagged polypeptide alternatively may be a cytokine or a growth factor or another soluble polypeptide that is capable of binding to an antigen of a target cell.

The term "adapter" or "adapter molecule" as used herein refers to a tagged polypeptide that can bind to an antigen of a target cell, e.g. antibody or antigen binding fragment thereof, and has bound thereto directly or indirectly at least one additional component, i.e. the tag. The adapter or adapter molecule may by a tagged antibody or antigen binding fragment thereof, a cytokine or a growth factor or another soluble polypeptide that is capable of binding to an antigen of a target cell. The retroviral vector particle specific for a tag as disclosed herein may bind to said adapter.

Such an adaptable retroviral vector system, that comprises a pseudotyped retroviral vector particle specific for a tag and said tag specific for an antigen expressed on the surface of a target cell is disclosed e.g. in WO2019086351A1.

The tag of said tagged polypeptide may be e.g. a hapten or dextran and the hapten or dextran may be bound by the antigen binding domain of the polypeptide comprising an antigen binding domain specific for the tag.

Haptens such as e.g. FITC, biotin, PE, streptavidin, thiamin or dextran are small molecules that elicit an immune response only when attached to a large carrier such as a protein; the carrier may be one that also does not elicit an immune response by itself. Once the body has generated antibodies to a hapten-carrier adduct, the small-molecule hapten may also be able to bind to the antibody, but it will usually not initiate an immune response; usually only the hapten-carrier adduct can do this.

The term "polypeptide comprising an antigen binding domain specific for a tag" as used herein refers to a polypeptide that can bind a tag of a tagged polypeptide. The tagged polypeptide is different from the polypeptide that comprises the antigen binding domain specific for the tag. The polypeptide comprising the antigen binding domain specific for a tag may be an antibody or antigen binding fragment thereof that binds to said tag of the tagged polypeptide.

The term "polypeptide comprising an antigen binding domain specific for CD62L" as used herein refers to a polypeptide that can bind to the antigen CD62L that is expressed on the surface of T cells expressing CD62L. The polypeptide comprising the antigen binding domain specific for CD62L may be an antibody or antigen binding fragment thereof that binds to said antigen CD62L.

The term "antibody" as used herein is used in the broadest sense to cover the various forms of antibody structures including but not being limited to monoclonal and polyclonal antibodies (including full length antibodies), multi-specific antibodies (e.g. bispecific antibodies), antibody fragments, i.e. antigen binding fragments of an antibody, immunoadhesins and antibody-immunoadhesin chimeras, that specifically recognize (i.e. bind) an antigen. "Antigen binding fragments" comprise a portion of a full-length antibody, preferably the variable domain thereof, or at least the antigen binding site thereof ("an antigen binding fragment of an antibody"). Examples of antigen binding fragments include Fab (fragment antigen binding), scFv (single chain fragment variable), single domain antibodies, diabodies, dsFv, Fab', single-chain antibody molecules, and multispecific antibodies formed from antibody fragments.

As used herein, the term "antigen" is intended to include substances that bind to or evoke the production of one or more antibodies and may comprise, but is not limited to, proteins, peptides, polypeptides, oligopeptides, lipids, carbohydrates such as dextran, and combinations thereof, for example a glycosylated protein or a glycolipid. The term "antigen" as used herein refers to a molecular entity that may be expressed on the surface of a target cell and that can be recognized by means of the adaptive immune system including but not restricted to antibodies or TCRs, or engineered molecules including but not restricted to endogenous or transgenic TCRs, CARs, scFvs or multimers thereof, Fab-fragments or multimers thereof, antibodies or multimers thereof, single chain antibodies or multimers thereof, or any other molecule that can execute binding to a structure with high affinity.

The term "expression" as used herein is defined as the transcription and/or translation of a particular nucleotide sequence driven by its promoter in a cell.

A recombinant protein is a biotechnologically generated protein that does not occur naturally in a eukaryotic and/or prokaryotic cell. Often it is composed of different domains from different proteins, e.g. as used herein, a viral envelope protein is fused (at its ectodomain) to a polypeptide that comprises an antigen binding domain specific for an antigen, e.g. CD62L or for a tag. Said polypeptide may be an antibody or antigen binding fragment thereof.

The term "T cells expressing CD62L" as used herein refers to T cell subsets of a specific phenotype. In general, T cells may be characterized based on their function and marker expression. Two main subgroups have been defined: CD4 expressing T cells (i.e. T helper cells) and CD8 expressing T cells (i.e. cytotoxic T cells). CD8 positive specifically lyse e.g. virus infected or tumor cells by releasing perforin, granzyme and FasL upon specific binding to the respective peptide presented on the MEC I to the TCR. On CD4+ T cells peptides presented on MEC II are bound specifically by the respective TCR inducing a signaling cascade triggering the release of several cytokines such as interferons and interleukins. Such cytokines may recruit other immune cells and may activate CD8+ T cells for a boosted and sustained cytolytic activity.

T cells differentiate into different phenotypes showing a specific memory or effector function profile.

Naïve T cells (T N) have recently undergone positive and negative selection in the thymus and are considered to be early differentiated with high memory function but a low effector function. They can be identified by flow cytometry expressing CD45RA, CCR7 and CD62L and being negative for CD45RO, CD95 and IL-2Rbeta. The terms "naïve T cells", resting T cells" and "non-activated T cells" may be used interchangeably.

Stem cell memory T cells ($T_{SCM}$) have a high potential for self-renewal, are minimally differentiated and can differentiate into other phenotypes. They can be identified by flow cytometry expressing CD45RA, CD45RO, CCR7, CD62L, CD95 and IL-2Rbeta.

Central memory T cells ($T_{CM}$) are characterized by a low effector function profile and a long persistence. Upon antigen encounter, this T cell subset expands rapidly and differentiate into T cells with effector function. They can be identified by flow cytometry expressing CD45RO, CCR7, CD62L, CD95 and IL-2Rbeta.

Effector memory T cells ($T_{EM}$) migrate to inflamed tissues and have an intermediate level of effector function. They can be identified by flow cytometry expressing CD45RO, CD95, IL-2Rbeta and being negative for CCR7 and CD62L.

Effector T cells ($T_{EFF}$) are short lived T cells with no memory function but the highest potential of cytolytic effector function. They can be identified by flow cytometry expressing CD45RA, CD95, IL-2Rbeta and being negative for CD45RO, CCR7 and CD62L.

CD62L (L-Selectin) is transmembrane protein mainly involved in lymphocyte homing of blood-borne T cells into secondary lymphoid organs such as lymph nodes by mediating binding of lymphocytes and endothelia. CD62L is expressed on monocytes, neutrophils, T and B cell subsets. On T cells, the expression of CD62L is regulated depending on the state of differentiation and activation as it is on $T_N$, $T_{SCM}$ and $T_{CM}$ only.

Upon engagement of the TCR, CD62L is proteolytically shed from the T-cell surface within hours by ADAM17 cleaving at a position very proximal to the membrane. It has been suggested that the CD62L downregulation is required to prevent activated T-cells re-entering lymph nodes from the bloodstream and allow entry into infected and inflamed tissues. The term "transgene" describes a segment of DNA containing a gene sequence that has been isolated from one organism and is introduced into a different organism. This non-native segment of DNA may either retain the ability to produce RNA or protein in the transgenic organism or alter the normal function of the transgenic organism's genetic code.

In general, a chimeric antigen receptor (CAR) may comprise an extracellular domain (extracellular part) comprising the antigen binding domain, a transmembrane domain and a cytoplasmic signaling domain (intracellular signaling domain). The extracellular domain may be linked to the transmembrane domain by a linker or spacer. The extracellular domain may also comprise a signal peptide. In some embodiments the CAR may be a adaptable CAR system (similar to the adaptable retroviral vector system) and may be then referred to as "anti-tag" CAR or "adapterCAR" or "universal CAR" as disclosed e.g. in U.S. Pat. No. 9,233,125 B2.

A "signal peptide" refers to a peptide sequence that directs the transport and localization of the protein within a cell, e.g. to a certain cell organelle (such as the endoplasmic reticulum) and/or the cell surface.

Generally, an "antigen binding domain" of a CAR refers to the region of the CAR that specifically binds to an antigen, e.g. to a tumor associated antigen (TAA) or tumor specific antigen (TSA). The CARs of the invention may comprise one or more antigen binding domains (e.g. a tandem CAR). Generally, the targeting regions on the CAR are extracellular. The antigen binding domain of the CAR may comprise an antibody or an antigen binding fragment thereof. The antigen binding domain of the CAR may comprise, for example, full length heavy chain, Fab fragments, single chain Fv (scFv) fragments, divalent single chain antibodies or diabodies. Any molecule that binds specifically to a given antigen such as affibodies or ligand binding domains from naturally occurring receptors may be used as an antigen binding domain. Often the antigen binding domain of a CAR is a scFv. Normally, in a scFv the variable regions of an immunoglobulin heavy chain and light chain are fused by a flexible linker to form a scFv. Such a linker may be for example the "(G$_4$S)$_3$-linker".

In some instances, it is beneficial for the antigen binding domain of the CAR to be derived from the same species in which the CAR will be used in. For example, when it is planned to use it therapeutically in humans, it may be beneficial for the antigen binding domain of the CAR to comprise a human or humanized antibody or antigen binding fragment thereof. Human or humanized antibodies or antigen binding fragments thereof can be made by a variety of methods well known in the art.

"Spacer" or "hinge" as used herein refers to the hydrophilic region which is between the antigen binding domain of the CAR and the transmembrane domain. The CARs of the invention may comprise an extracellular spacer domain but is it also possible to leave out such a spacer. The spacer may include e.g. Fc fragments of antibodies or fragments thereof, hinge regions of antibodies or fragments thereof, CH2 or CH3 regions of antibodies, accessory proteins, artificial spacer sequences or combinations thereof. A prominent example of a spacer is the CD8 alpha hinge.

The transmembrane domain of the CAR may be derived from any desired natural or synthetic source for such domain. When the source is natural the domain may be derived from any membrane-bound or transmembrane protein. The transmembrane domain may be derived for example from CD8alpha or CD28. When the key signaling and antigen recognition modules (domains) are on two (or even more) polypeptides then the CAR may have two (or more) transmembrane domains. Splitting key signaling and antigen recognition modules enable for a small molecule-dependent, titratable and reversible control over CAR cell expression (e.g. WO2014127261A1) due to small molecule-dependent heterodimerizing domains in each polypeptide of the CAR.

The cytoplasmic signaling domain (the intracellular signaling domain or the activating endodomain) of the CAR is responsible for activation of at least one of the normal effector functions of the immune cell in which the CAR is expressed, if the respective CAR is an activating CAR (normally, a CAR as described herein refers to an activating CAR). "Effector function" means a specialized function of a cell, e.g. in a T cell an effector function may be cytolytic activity or helper activity including the secretion of cytokines. The intracellular signaling domain refers to the part of a protein which transduces the effector function signal and directs the cell expressing the CAR to perform a specialized function. The intracellular signaling domain may include any complete, mutated or truncated part of the intracellular signaling domain of a given protein sufficient to transduce a signal which initiates or blocks immune cell effector functions.

Prominent examples of intracellular signaling domains for use in the CARs include the cytoplasmic signaling sequences of the T cell receptor (TCR) and co-receptors that initiate signal transduction following antigen receptor engagement.

Generally, T cell activation can be mediated by two distinct classes of cytoplasmic signaling sequences, firstly those that initiate antigen-dependent primary activation through the TCR (primary cytoplasmic signaling sequences, primary cytoplasmic signaling domain) and secondly those that act in an antigen-independent manner to provide a secondary or co-stimulatory signal (secondary cytoplasmic signaling sequences, co-stimulatory signaling domain). Therefore, an intracellular signaling domain of a CAR may comprise one or more primary cytoplasmic signaling domains and/or one or more secondary cytoplasmic signaling domains.

Primary cytoplasmic signaling domains that act in a stimulatory manner may contain ITAMs (immunoreceptor tyrosine-based activation motifs). Examples of ITAM containing primary cytoplasmic signaling domains often used in CARs are that those derived from TCRζ (CD3ζ), FcRgamma, FcRbeta, CD3gamma, CD3delta, CD3epsilon, CD5, CD22, CD79a, CD79b, and CD66d. Most prominent is sequence derived from CD3ζ.

The cytoplasmic domain of the CAR may be designed to comprise the CD3ζ signaling domain by itself or combined with any other desired cytoplasmic domain(s). The cytoplasmic domain of the CAR can comprise a CD3ζ chain portion and a co-stimulatory signaling region (domain). The co-stimulatory signaling region refers to a part of the CAR comprising the intracellular domain of a co-stimulatory molecule. A co-stimulatory molecule is a cell surface molecule other than an antigen receptor or their ligands that is required for an efficient response of lymphocytes to an antigen. Examples for a co-stimulatory molecule are CD27, CD28, 4-1BB (CD137), OX40, CD30, CD40, PD-1, ICOS, lymphocyte function-associated antigen-1 (LFA-1), CD2, CD7, LIGHT, NKG2C, B7-H3.

The cytoplasmic signaling sequences within the cytoplasmic signaling part of the CAR may be linked to each other with or without a linker in a random or specified order. A short oligo- or polypeptide linker, which is preferably between 2 and 10 amino acids in length, may form the linkage. A prominent linker is the glycine-serine doublet.

As an example, the cytoplasmic domain may comprise the signaling domain of CD3ζ and the signaling domain of CD28. In another example the cytoplasmic domain may comprise the signaling domain of CD3ζ and the signaling domain of CD137. In a further example, the cytoplasmic domain may comprise the signaling domain of CD3ζ, the signaling domain of CD28, and the signaling domain of CD137.

If the CAR is an inhibitory CAR (referred to normally as "iCAR"), then said CAR may have the same extracellular and/or transmembrane domains as the activating CAR but differs from the activating CAR with regard to the endodmain. The at least one endodomain of the inhibitory CAR may be a cytoplasmic signaling domain comprising at least one signal transduction element that inhibits an immune cell or comprising at least one element that induces apoptosis.

The CARs that may be transduced by the pseudotyped retroviral vector particle as disclosed herein present may be designed to comprise any portion or part of the above-mentioned domains as described herein in any order and/or combination resulting in a functional CAR.

EXAMPLES

Example 1: Construction of CD62L Specific LVs

Figure 3A:
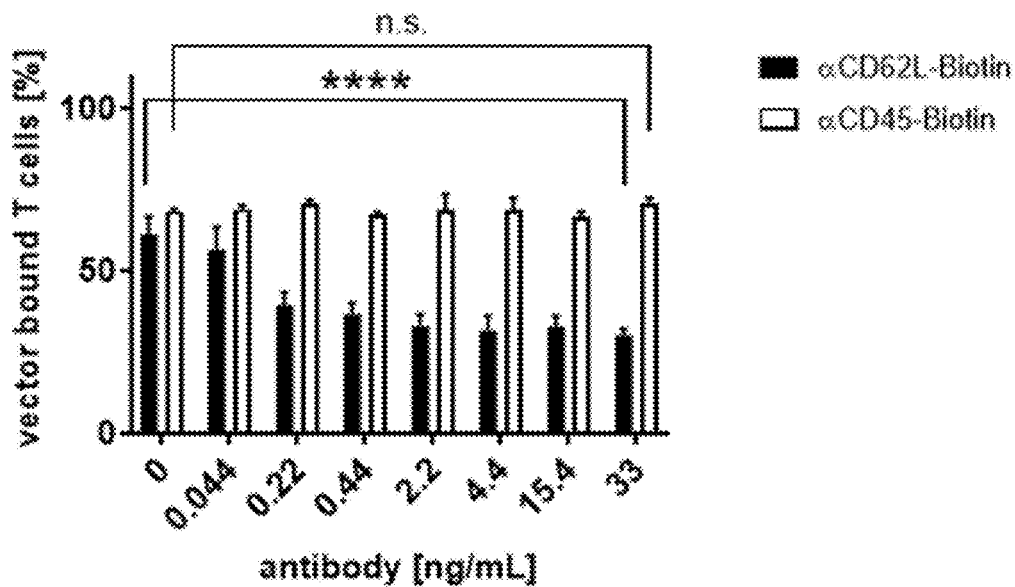
FIGS. 3A and 3B: Confirming selectivity of CD62L-LV with antibody blocking experiments on PBMCs. Activated PBMC were preincubated at 4° C. without or with increasing concentrations of a CD62L specific antibody (black bars). After 1 h, 10 µl of CD62L-LV were added for 30 min at 4° C. followed by the detection of cell bound LV by flow cytometry. The ratio of cells with cell bound CD62L-LV (left) and the relative amount of bound CD62L-LV per cell (right; MFI) is depicted. As (negative) control non-related Biotin-tagged CD45-specific antibody was used in the same concentrations (white bars).
Figure 3B:
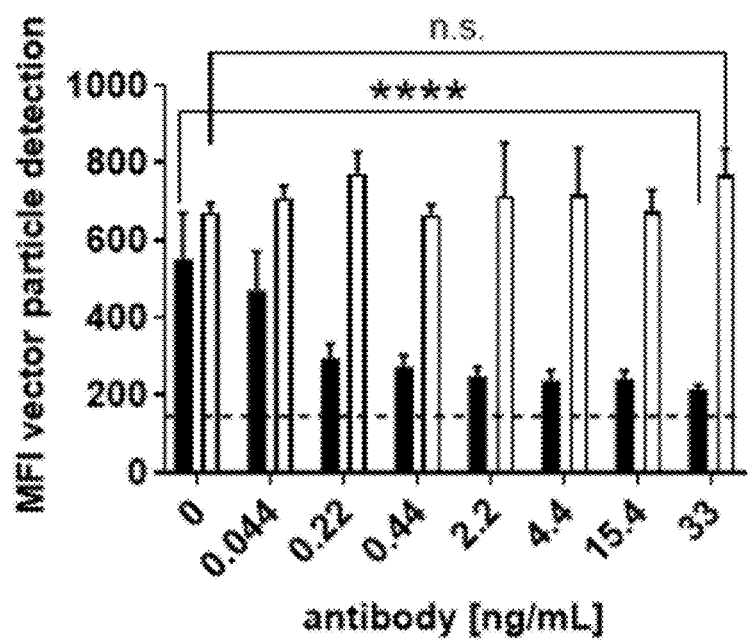

CD62L-specific pseudotyped lentiviral vectors (CD62L-LV) are generated by engineering envelope proteins that are used for pseudotyping. The two envelope proteins within the Paramyxoviridae family have distinct functions. The protein H, HN or G with antigen binding activity mediates binding to specific cellular receptor. Upon binding the protein with fusion activity mediates fusion of the viral and cellular membrane and entry of the viral capsid into the cytoplasm. A protein with antigen binding activity is rendered CD62L specific by reducing or ablating interaction with the native receptors and equipping it with a polypeptide such as a scFv, that is specific for CD62L. For lentiviral vectors that are pseudotyped with measles virus envelope proteins, the H protein is truncated at the cytoplasmatic domain and mutated at positions 481, 533, 548, 549 that are crucial for receptor binding. A polypeptide such as a CD62L specific scFv is added at the C-terminal part of the H protein. Alternatively, indirect, adaptable targeting systems are available that require a tagged adapter molecule to mediate specific binding to the target antigen and selective transduction. The polypeptide that is fused to the protein with antigen binding activity is specific for a tag of the tagged polypeptide and said tagged polypeptide specifically binds to the antigen expressed on the surface of a target cell. The tag is biotin or dextran and the tagged polypeptide may be an antibody or fragment thereof that is labelled with biotin or dextran.

The polypeptide specific for CD62L (direct approach) or for the tag (indirect adapter) may be an antibody fragment such as an scFv.

Two chains of the scFvs are linked via a (G4S) 3 linker (SEQ ID NO:9) and may be present in either orientations (VH-VL or VL-VH). The orientation can influence expression levels, stability, affinity and the titer of the pseudotyped retroviral vector or virus-like particle thereof, respectively. A His tag (SEQ ID NO: 12) has been added to the C-terminal end of the protein with antigen binding activity protein, to enable measuring surface expression by flow cytometry (FIG. 2).

DNA encoding the scFv of the CD62L, dextran or biotin specific antibody in VH-VL orientation were obtained by gene synthesis (ATUM, Newark, California). Flanking restrictions sites SfiI and NotI were inserted to enable insertion into the SfiI and NotI digested Hmut encoding plasmid pCG-Hmut (Anliker et al. (2010)). DNA encoding the scFv in VL-VH orientation was obtained by PCR using a plasmid encoding for the scFv in VL-VH orientation with primers adding the restriction sites. The amplified scFv was inserted via SfiI and NotI into the digested Hmut encoding plasmid.

Example 2: Generation of CD62L-LV

Pseudotyped retroviral vector particles specific for CD62L were generated by transient transfection of HEK-293T cells. HEK-293T cells that were seeded in T175 flasks in DMEM/10% FBS the day before were transfected using PEI (Polyethyleneimine, branched 25 kDa, Sigma Aldrich) transfection with a composition of a plasmid encoding for the H protein, a plasmid encoding for the F protein, a packaging plasmid encoding gag/pol/rev and a psi-positive transfer vector plasmid encoding a polycistronic CD19-specific CAR cassette linked via F2A site to the LNGFR marker protein. A total of 35 μg DNA as a mixture of all aforementioned plasmids were diluted in 2.3 mL DMEM per T175 flask and vortexed for 20 sec. In parallel, per flask 140 μL of branched PEI (Sigma-Aldrich) was diluted in 2.2 mL DMEM and vortexed for 20 sec. The DNA containing solution and the PEI containing solution were combined, vortexed for 20 sec and incubated for 10 min at RT. The medium on HEK 293T cells was exchanged for 10 mL DMEM+15 FBS and 3 mM L-Glutamine. 4.7 mL of the transfection reaction mix were added onto each T175 flask. Flasks were shaken slightly and incubated at 37° C. for either 6 h or overnight. Next, the medium was aspirated and 14 mL DMEM comp was added per flask.

Two days after transfection, the vector particles were harvested. For that purpose, supernatant of the T175 flasks was collected and filtered through a 0.45 μm filter. The supernatant of 10 flasks was pooled in a VWR centrifuge bucket and 9 mL of PBS+20% sucrose was underlain. Centrifugation was performed at 4500 rpm and 4° C. for 24 h. Afterwards, the supernatant was discarded. Per T175 flask used, 60 μL of cold PBS was put onto the pellet and pellet was resuspended by pipetting up and down five times. For further resolving the pellet, tubes were shaken at 4° C. and 20 rpm for 1 h. The pellet was finally resuspended by pipetting up and down 60 times. Vector stock was aliquoted to 30 μL and frozen at −80° C.

Example 3: Titration of CD62L-LV

Titration of the CD62L-LV was performed on recombinant HT1080 cells expressing CD62L and aHis-HT1080 cells. 8000 cells were seeded in a 96-well plate in 100 μL RPMI containing 10% FBS and 3 mM L-Glutamine. A dilution series with the five dilutions and a dilution factor of 5 was produced. Thereby, the start point was a 1:20 dilution. 100 μL of these dilutions were added on the cells and incubated for four days. That procedure resulted in the following absolute amounts of vector stock added onto the cells: 1st dilution: 5 μL; 2nd dilution: 1 μL; 3rd dilution: 0.2 μL; 4th dilution: 0.04 μL; 5th dilution: 0.008 μL. For analysis, medium was discarded, and cells were detached with 50 μL PBS+1 mM EDTA. Cells were incubated at 37° C. until they were detached. 50 μL PBS was added and cells were resuspended. Cells were transferred into FACS tubes and percentage of transduced cells was detected via flow cytometry by staining against LNGFR. Calculation of the titer was performed with the formula: Transducting Units/mL=(transgene positive cells [%])×(8000)×(volume of applied vector stock [mL]).

Example 4: Selective Transduction of CD62L-Expressing Cells

8000 HT1080 cells or recombinant HT1080 cells expressing CD62L were seeded in a 96-well plate in 100 μL RPMI containing 10% FBS and 3 mM L-Glutamine and transduced with GFP-encoding CD62L-LV or the same dose of VSV-G-LV as control. 4 days after adding lentiviral vectors particles, the transduced cells were harvested and the transduction efficiency was determined by flow cytometry for GFP expression (FIG. 2).

Example 5: Specificity of CD62L-LV on PBMC

CD62L is expressed on naive T cells, stem cell memory and central memory T cells. A combination of a competition and binding assay was performed with CD62L-LV and a CD62L specific antibody derived from the same clone to show the specificity of CD62L-LV. When CD62L-LV and the antibody are combined in one sample with CD62L expressing cells, both compete for the binding to the same epitope of CD62L. Cells were incubated with different concentrations of the parental antibody for 1 h at 4° C., and then CD62L-LV particles were added for 30 min at 4° C. followed by a FACS staining gated on T cells to detect bound vector particles. The vector particles bound to the surface of T cells were detected via CD3 and LNGFR staining. As negative control a CD45 antibody at the same concentrations was applied (FIG. 3)

Example 6: Quantification of Shed CD62L in the Supernatant of PBMC

Figure 4:
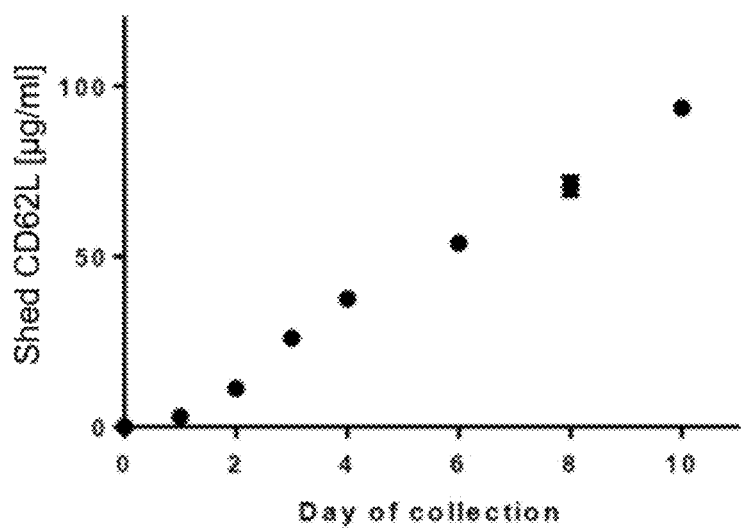
FIG. 4: Accumulation of shed CD62L in the supernatant of T cells over time as determined by ELISA.

Frozen PBMC were thawed, fully activated with 1 μg/mL CD3 specific antibody (OKT3) and 3 μg/mL of a CD28 specific antibody in T cell medium containing IL-7 and IL-15. No medium exchange or splitting was performed on these PBMC during cultivation. At day 2, 3, 6, 8 and 10, the whole supernatant of one well was collected and frozen at −80° C. For day 0, TCM medium containing IL-7 and IL-15 was placed into a well which was coated with aCD3 and incubated overnight at 37° C. and then frozen at −80° C. Afterwards the presence as well as the concentration of shed CD62L (sCD62L) was determined using a commercially available ELISA kit for sCD62L (R&D Systems). All samples were measured in technical duplicates, including the standard. Supernatants collected at day 2, 3, 6, 8 and 10 were diluted 1:10 in TCM medium (FIG. 4).

Example 7: Influence of Shed CD62L on Cellular Binding of CD62L-LV

Figure 5:
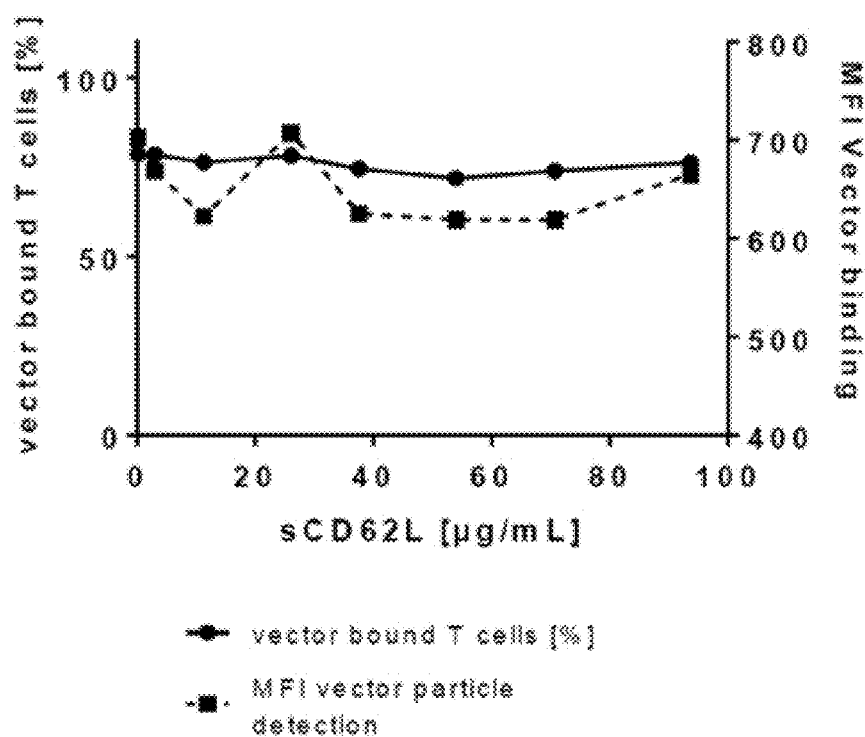
FIG. 5: No inhibitory effect of shed CD62L on the binding ability of CD62L-LV. 100 of CD62L-LV were preincubated for 1 h at 4° C. with 40 µl conditioned medium containing a defined concentration of shed CD62L (sCD62L). The mixture was applied to activated PBMC for 30 min at 4° C. followed by the detection of cell bound LV by flow cytometry. The ratio of cells with cell bound CD62L-LV (solid line) and the relative amount of bound CD62L-LV per cell (dashed line; MFI) is depicted.

The influence of sCD62L on binding of CD62L-LV onto its target was investigated by detecting cell bound LVs on activated PBMC in the presence of conditioned media containing different concentrations of sCD62L. Frozen PBMC were thawed, fully activated by incubation with 1 μg/mL CD3 specific antibody (OKT3) and 3 μg/mL of a CD28 specific antibody in T cell medium containing IL-7 and IL-15 for 2 days. 10 μL of CD62L-LV were incubated with 40 μL of conditioned medium containing a defined concentration of sCD62L for 1 h at 4° C. The mixture of conditioned medium and vector stock was then added to 40,000 PBMC seeded in a 96-well plate in a total volume of 100 μL media supplemented with IL-7 and IL-15 for 30 min at 4° C. Binding of the vector particle was quantified via flow cytometry by detecting cell bound CD62L-LV upon staining of LNGFR (co-displayed on the LV surface) on viable T cells (CD3+ cells) (FIG. 5).

Example 8: Transduction of PBMC with CD62L-LV in the Presence of Shed CD62L

Figure 6:
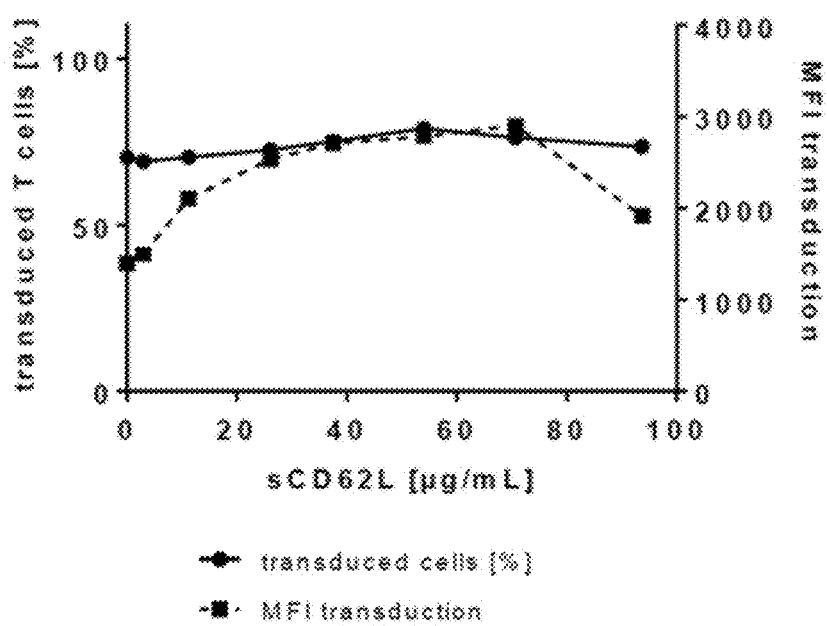
FIG. 6: No inhibitory effect of shed CD62L on the transduction activity of CD62L-LV. Activated PBMC were seeded in 50 µL of conditioned medium containing increasing concentrations of sCD62L. 10 µL of CD62L-LV in the presence of the transduction enhancer Vectofusin-1 were added and centrifuged at 850×g for 90 min at 32° C. 100 µL of conditioned medium was added and flow cytometry analysis was performed 5 days after transduction. The ratio of transduced T cells expressing the transgene (in %, solid line) and the relative expression levels (dashed line) are depicted as MFI. Shed CD62L had no negative impact on transduction efficiency of CD62L-LV.

Frozen PBMC were thawed, fully activated by incubation with 1 μg/mL CD3 specific antibody (OKT3) and 3 μg/mL of a CD28 specific antibody in T cell medium containing IL-7 and IL-15 for 2 days. PBMC were seeded in 50 μL conditioned medium containing different concentrations of sCD62L. Transduction was performed in form of spinfection at 850×g for 90 min at 32° C. using 10 μL of the CD62L-LV vector stock. After spinfection 100 μL of conditioned medium containing defined concentrations of sCD62L was added. Three days later 100 μL of the supernatant was replaced by 100 μL fresh TCM containing IL-7 and IL-15. FACS staining was performed after two more days and the percentage of LNGFR expressing T cells as well as the MFI was determined. (FIG. 6)

The invention claimed is:

1. A composition comprising:
   i) a pseudotyped retroviral vector particle that expresses:
      a) a first envelope protein of a Paramyxoviridae family virus that has antigen binding activity, wherein the first envelope protein is selected from protein G, protein HN and protein H;
         wherein the first envelope protein has been modified whereby it does not bind to naturally occurring receptors for said virus on host cells,
         wherein said first envelope protein is fused at its ectodomain to an antigen binding domain that specifically binds antigen CD62L;
      b) a second envelope protein of said Paramyxoviridae family virus that has fusion activity;
      wherein the composition further comprises:
   ii) T cells expressing CD62L.

2. The composition according to claim 1, wherein said T cells expressing CD62L comprise central memory T (TCM) cells, and/or stem memory T (TSCM) cells, and/or naïve T cells.

3. The composition according to claim 1, wherein said composition comprises TCM cells, TSCM cells, naïve T cells, effector T (TEF) cells, and effector memory T (TEM) cells.

4. The composition according to claim 1, wherein said Paramyxoviridae virus is a virus of the Morbillivirus genus or the Henipavirus genus.

5. The composition according to claim 1, wherein said first envelope protein lacks at least one part of the cytoplasmic region of said protein G, said protein HN, or said protein H.

6. The composition according to claim 1, wherein said second envelope protein has been modified whereby it lacks at least a part of the cytoplasmic region of said second envelope protein.

7. The composition according to claim 1, wherein said antigen binding domain specific for CD62L is a single chain variable region (scFv).

8. The composition according to claim 1, wherein said antigen binding domain specific for CD62L comprises the amino acid sequence of SEQ ID NO:1 SEQ ID NO:2, SEQ ID NO:3, SEQ ID NO:4, SEQ ID NO:5 and SEQ ID NO:6.

9. The composition according to claim 1, wherein said antigen binding domain specific for CD62L comprises the amino acid sequence of SEQ ID NO:7 and SEQ ID NO:8.

10. The composition according to claim 1, wherein said retroviral vector particle comprises a transgene.

11. The composition according to claim 10, wherein said transgene encodes a chimeric antigen receptor.

12. A composition comprising:

i) a pseudotyped retroviral vector particle that expresses:

a) a first envelope protein of a Paramyxoviridae family virus that has antigen binding activity, wherein the first envelope protein is selected from protein G, protein HN and protein H;

wherein the first envelope protein has been modified whereby it does not bind to naturally occurring receptors for said virus on host cells, wherein said first envelope protein is fused at its ectodomain to an antigen binding domain that specifically binds a tag of a tagged polypeptide;

b) a second envelope protein of said Paramyxoviridae family virus that has fusion activity;

ii) T cells expressing cell-surface CD62L, and iii) said tagged polypeptide, wherein said tagged polypeptide binds specifically to CD62L.

13. A method for transducing T cells that express cell surface CD62L, the method comprising contacting said T cells in a medium with a pseudotyped retroviral vector particle, wherein the pseudotyped retroviral vector particle expresses:

a) a first envelope protein of a Paramyxoviridae family virus that has antigen binding activity, wherein the first envelope protein is selected from protein G, protein HN and protein H;

wherein the first envelope protein has been modified whereby it does not bind to naturally occurring receptors for said virus on host cells, wherein said first envelope protein is fused at its ectodomain to an antigen binding domain that specifically binds CD62L; and b) a second envelope protein of said Paramyxoviridae family virus that has fusion activity;

whereupon said T cells are transduced by the pseudotyped retroviral vector particle, irrespective of whether shed CD62L (sCD62L) is present in the medium.

14. A method for transducing T cells that express cell-surface CD62L, the method comprising contacting said T cells in a medium with a pseudotyped retroviral vector particle and with a tagged polypeptide that specifically binds CD62L, wherein the pseudotyped retroviral vector particle expresses:

a) a first envelope protein of a Paramyxoviridae family virus that has antigen binding activity, wherein the first envelope protein is selected from protein G, protein HN and protein H;

wherein the first envelope protein has been modified whereby it does not bind to naturally occurring receptors for said virus on host cells, wherein said first envelope protein is fused at its ectodomain to an antigen binding domain that specifically binds a tag on said tagged polypeptide; and b) a second envelope protein of said Paramyxoviridae family virus that has fusion activity;

whereupon said T cells are transduced by the pseudotyped retroviral vector particle, irrespective of whether shed CD62L (sCD62L) is present in the medium.

* * * * *

SEQUENCE LISTING

```
<160> NUMBER OF SEQ ID NOS: 18

<210> SEQ ID NO 1
<211> LENGTH: 15
<212> TYPE: PRT
<213> ORGANISM: Artificial sequence
<220> FEATURE:
<223> OTHER INFORMATION: CDR1 of VL of anti-CD62L (Kabat definition)

<400> SEQUENCE: 1

Lys Ala Ser Gln Ser Val Asp Tyr Asp Gly Asp Ser Tyr Met Asn
1               5                   10                  15

<210> SEQ ID NO 2
<211> LENGTH: 7
<212> TYPE: PRT
<213> ORGANISM: Artificial sequence
<220> FEATURE:
<223> OTHER INFORMATION: CDR2 of VL of anti-CD62L (Kabat definition)

<400> SEQUENCE: 2

Ala Ala Ser Asn Leu Glu Ser
1               5

<210> SEQ ID NO 3
<211> LENGTH: 9
<212> TYPE: PRT
<213> ORGANISM: Artificial sequence
<220> FEATURE:
<223> OTHER INFORMATION: CDR3 of VL of anti-CD62L (Kabat definition)
```

```
<400> SEQUENCE: 3

Gln Gln Ser Asn Glu Asp Pro Tyr Thr
1               5

<210> SEQ ID NO 4
<211> LENGTH: 5
<212> TYPE: PRT
<213> ORGANISM: Artificial sequence
<220> FEATURE:
<223> OTHER INFORMATION: CDR1 of VH of anti-CD62L (Kabat definition)

<400> SEQUENCE: 4

Ser Tyr Ala Met Ser
1               5

<210> SEQ ID NO 5
<211> LENGTH: 16
<212> TYPE: PRT
<213> ORGANISM: Artificial sequence
<220> FEATURE:
<223> OTHER INFORMATION: CDR2 of VH of anti-CD62L (Kabat definition)

<400> SEQUENCE: 5

Ser Ile Ser Ser Gly Gly Ser Thr Tyr Tyr Pro Asp Ser Val Lys Gly
1               5                   10                  15

<210> SEQ ID NO 6
<211> LENGTH: 8
<212> TYPE: PRT
<213> ORGANISM: Artificial sequence
<220> FEATURE:
<223> OTHER INFORMATION: CDR3 of VH of anti-CD62L (Kabat definition)

<400> SEQUENCE: 6

Asp Asp Asp Gly Tyr Tyr Asp Tyr
1               5

<210> SEQ ID NO 7
<211> LENGTH: 111
<212> TYPE: PRT
<213> ORGANISM: Artificial sequence
<220> FEATURE:
<223> OTHER INFORMATION: VL of anti-CD62L

<400> SEQUENCE: 7

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

<210> SEQ ID NO 8
<211> LENGTH: 116
```

```
<212> TYPE: PRT
<213> ORGANISM: Artificial sequence
<220> FEATURE:
<223> OTHER INFORMATION: VH of anti-CD62L

<400> SEQUENCE: 8

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
            85                  90                  95

Arg Asp Asp Asp Gly Tyr Tyr Asp Tyr Trp Gly Gln Gly Thr Thr Leu
            100                 105                 110

Thr Val Ser Ser
        115

<210> SEQ ID NO 9
<211> LENGTH: 242
<212> TYPE: PRT
<213> ORGANISM: Artificial sequence
<220> FEATURE:
<223> OTHER INFORMATION: scFv of anti-CD62L (e.g. in heavy light
      orientation with (G4S)3 linker)

<400> SEQUENCE: 9

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
            85                  90                  95

Arg Asp Asp Asp Gly Tyr Tyr Asp Tyr Trp Gly Gln Gly Thr Thr Leu
            100                 105                 110

Thr Val Ser Ser Gly Gly Gly Gly Ser Gly Gly Gly Gly Ser Gly Gly
            115                 120                 125

Gly Gly Ser Asp Ile Val Leu Thr Gln Ser Pro Ala Ser Leu Ala Val
        130                 135                 140

Ser Leu Gly Gln Arg Ala Thr Ile Ser Cys Lys Ala Ser Gln Ser Val
145                 150                 155                 160

Asp Tyr Asp Gly Asp Ser Tyr Met Asn Trp Tyr Gln Gln Lys Pro Gly
            165                 170                 175

Gln Pro Pro Lys Leu Leu Ile Tyr Ala Ala Ser Asn Leu Glu Ser Gly
            180                 185                 190
```

Ile Pro Ala Arg Phe Ser Gly Ser Gly Ser Gly Thr Asp Phe Thr Leu
            195                 200                 205

Asn Ile His Pro Val Glu Glu Asp Ala Ala Thr Tyr Tyr Cys Gln
210                 215                 220

Gln Ser Asn Glu Asp Pro Tyr Thr Phe Gly Gly Gly Thr Lys Leu Glu
225                 230                 235                 240

Ile Lys

<210> SEQ ID NO 10
<211> LENGTH: 317
<212> TYPE: PRT
<213> ORGANISM: Artificial sequence
<220> FEATURE:
<223> OTHER INFORMATION: sCD62L (Uniprot ID P14151-1)

<400> SEQUENCE: 10

Met Ile Phe Pro Trp Lys Cys Gln Ser Thr Gln Arg Asp Leu Trp Asn
1               5                   10                  15

Ile Phe Lys Leu Trp Gly Trp Thr Met Leu Cys Cys Asp Phe Leu Ala
            20                  25                  30

His His Gly Thr Asp Cys Trp Thr Tyr His Tyr Ser Glu Lys Pro Met
        35                  40                  45

Asn Trp Gln Arg Ala Arg Arg Phe Cys Arg Asp Asn Tyr Thr Asp Leu
    50                  55                  60

Val Ala Ile Gln Asn Lys Ala Glu Ile Glu Tyr Leu Glu Lys Thr Leu
65                  70                  75                  80

Pro Phe Ser Arg Ser Tyr Tyr Trp Ile Gly Ile Arg Lys Ile Gly Gly
                85                  90                  95

Ile Trp Thr Trp Val Gly Thr Asn Lys Ser Leu Thr Glu Glu Ala Glu
            100                 105                 110

Asn Trp Gly Asp Gly Glu Pro Asn Asn Lys Asn Lys Glu Asp Cys
        115                 120                 125

Val Glu Ile Tyr Ile Lys Arg Asn Lys Asp Ala Gly Lys Trp Asn Asp
130                 135                 140

Asp Ala Cys His Lys Leu Lys Ala Ala Leu Cys Tyr Thr Ala Ser Cys
145                 150                 155                 160

Gln Pro Trp Ser Cys Ser Gly His Gly Glu Cys Val Glu Ile Ile Asn
                165                 170                 175

Asn Tyr Thr Cys Asn Cys Asp Val Gly Tyr Tyr Gly Pro Gln Cys Gln
            180                 185                 190

Phe Val Ile Gln Cys Glu Pro Leu Glu Ala Pro Glu Leu Gly Thr Met
        195                 200                 205

Asp Cys Thr His Pro Leu Gly Asn Phe Ser Phe Ser Ser Gln Cys Ala
    210                 215                 220

Phe Ser Cys Ser Glu Gly Thr Asn Leu Thr Gly Ile Glu Glu Thr Thr
225                 230                 235                 240

Cys Gly Pro Phe Gly Asn Trp Ser Ser Pro Glu Pro Thr Cys Gln Val
                245                 250                 255

Ile Gln Cys Glu Pro Leu Ser Ala Pro Asp Leu Gly Ile Met Asn Cys
            260                 265                 270

Ser His Pro Leu Ala Ser Phe Ser Phe Thr Ser Ala Cys Thr Phe Ile
        275                 280                 285

Cys Ser Glu Gly Thr Glu Leu Ile Gly Lys Lys Lys Thr Ile Cys Glu
        290                 295                 300

```
Ser Ser Gly Ile Trp Ser Asn Pro Ser Pro Ile Cys Gln
305                 310                 315
```

```
<210> SEQ ID NO 11
<211> LENGTH: 5
<212> TYPE: PRT
<213> ORGANISM: Artificial sequence
<220> FEATURE:
<223> OTHER INFORMATION: measles virus (Edmonston strain); transmembrane
      domain of F protein

<400> SEQUENCE: 11

Leu Ile Cys Cys Cys
1               5
```

```
<210> SEQ ID NO 12
<211> LENGTH: 4
<212> TYPE: PRT
<213> ORGANISM: Artificial sequence
<220> FEATURE:
<223> OTHER INFORMATION: measles virus (Edmonston strain); Name:
      transmembrane domain of H protein

<400> SEQUENCE: 12

Pro Tyr Val Leu
1
```

```
<210> SEQ ID NO 13
<211> LENGTH: 33
<212> TYPE: PRT
<213> ORGANISM: Artificial sequence
<220> FEATURE:
<223> OTHER INFORMATION: measles virus (Edmonston strain); cytoplasmic
      domain of F protein

<400> SEQUENCE: 13

Arg Gly Arg Cys Asn Lys Lys Gly Glu Gln Val Gly Met Ser Arg Pro
1               5                   10                  15

Gly Leu Lys Pro Asp Leu Thr Gly Thr Ser Lys Ser Tyr Val Arg Ser
            20                  25                  30

Leu
```

```
<210> SEQ ID NO 14
<211> LENGTH: 34
<212> TYPE: PRT
<213> ORGANISM: Artificial sequence
<220> FEATURE:
<223> OTHER INFORMATION: measles virus (Edmonston strain); cytoplasmic
      domain of H protein

<400> SEQUENCE: 14

Met Ser Pro Gln Arg Asp Arg Ile Asn Ala Phe Tyr Lys Asp Asn Pro
1               5                   10                  15

His Pro Lys Gly Ser Arg Ile Val Ile Asn Arg Glu His Leu Met Ile
            20                  25                  30

Asp Arg
```

```
<210> SEQ ID NO 15
<211> LENGTH: 21
<212> TYPE: PRT
<213> ORGANISM: Artificial sequence
<220> FEATURE:
<223> OTHER INFORMATION: Nipah Virus; transmembrane domain of G protein
```

```
<400> SEQUENCE: 15

Phe Asn Thr Tyr Ile Ala Leu Leu Gly Ser Ile Val Ile Ile Val Met
1               5                   10                  15

Asn Ile Met Ile Ile
            20

<210> SEQ ID NO 16
<211> LENGTH: 45
<212> TYPE: PRT
<213> ORGANISM: Artificial sequence
<220> FEATURE:
<223> OTHER INFORMATION: Nipah Virus; cytoplasmic domain of G protein

<400> SEQUENCE: 16

Met Pro Ala Glu Asn Lys Lys Val Arg Phe Glu Asn Thr Thr Ser Asp
1               5                   10                  15

Lys Gly Lys Ile Pro Ser Lys Val Ile Lys Ser Tyr Tyr Gly Thr Met
            20                  25                  30

Asp Ile Lys Lys Ile Asn Glu Gly Leu Leu Asp Ser Lys
            35                  40                  45

<210> SEQ ID NO 17
<211> LENGTH: 21
<212> TYPE: PRT
<213> ORGANISM: Artificial sequence
<220> FEATURE:
<223> OTHER INFORMATION: Nipah Virus; transmembrane domain of F protein

<400> SEQUENCE: 17

Tyr Val Leu Ser Ile Ala Ser Leu Cys Ile Gly Leu Ile Thr Phe Ile
1               5                   10                  15

Ser Phe Ile Ile Val
            20

<210> SEQ ID NO 18
<211> LENGTH: 28
<212> TYPE: PRT
<213> ORGANISM: Artificial sequence
<220> FEATURE:
<223> OTHER INFORMATION: Nipah Virus; cytoplasmic domain of F protein

<400> SEQUENCE: 18

Glu Lys Lys Arg Asn Thr Tyr Ser Arg Leu Glu Asp Arg Arg Val Arg
1               5                   10                  15

Pro Thr Ser Ser Gly Asp Leu Tyr Tyr Ile Gly Thr
            20                  25
```